United States Patent [19]

Sawayanagi et al.

[11] Patent Number: 4,948,581
[45] Date of Patent: Aug. 14, 1990

[54] LONG ACTING DICLOFENAC SODIUM PREPARATION

[75] Inventors: Yoichi Sawayanagi, Shibuya; Yoshiharu Otani, Yokohama, both of Japan

[73] Assignee: Dojin Iyaku-Kako Co., Ltd., Tokyo, Japan

[21] Appl. No.: 311,333

[22] Filed: Feb. 15, 1989

[51] Int. Cl.⁵ .................... A61K 31/78; A61N 37/12
[52] U.S. Cl. ........................................ 424/81; 514/567
[58] Field of Search ...................... 424/78, 81; 514/567

[56] References Cited

U.S. PATENT DOCUMENTS 4,798,724  1/1989  Khanna ................................ 424/81

FOREIGN PATENT DOCUMENTS 44811  3/1986  Japan .

Primary Examiner—Joseph L. Schofer
Assistant Examiner—Peter F. Kulkosky
Attorney, Agent, or Firm—Oliff & Berridge

[57] ABSTRACT

A diclofenac sodium preparation comprising a rapidly soluble component including an active ingredient consisting essentially of diclofenac sodium, and an enteric component including an active ingredient consisting essentially of diclofenac sodium and an enteric coating therefor provides prolonged action when the enteric coating is formed from a mixture comprising 100 parts by weight of a methacrylic acid-methyl methacrylate copolymer, 3–40 parts by weight of a glycerin fatty acid ester, and 1-150 parts by weight of talc.

9 Claims, 2 Drawing Sheets

LONG ACTING DICLOFENAC SODIUM PREPARATION

BACKGROUND OF THE INVENTION

This invention relates to a long acting diclofenac sodium preparation, and more particularly, to a long acting diclofenac sodium preparation in which a rapidly soluble component is combined with an enteric component having an enteric coating to provide prolonged action.

Diclofenac sodium or sodium 2-(2,6-dichloroanilino)-phenylacetate belonging to a class of non-steroid drugs has as high antiinflammatory, analgesic and antipyretic actions as indomethacin. Highly evaluated for its effectiveness, diclofenac sodium has been widely used clinically in the form of tablets and suppositories.

It is generally known that diclofenac sodium migrates into blood within 30 minutes and reaches the maximum concentration in blood within 2 hours after oral administration and the blood concentration half life is as short as 1.3 hours. Since diclofenac sodium is quickly absorbed in and excreted from blood, it is difficult to maintain in blood for a long time. For this reason, currently commercially available diclofenac sodium tablets must be taken three times a day. In addition, it has been reported that oral administration of diclofenac sodium would often induce various side effects including gastroenteritis. Therefore, there is a strong need for a long acting preparation which can sustain the action of diclofenac sodium in safe over an extended period of time.

Japanese Patent Application Kokai No. 61-44811 (laid open Mar. 4, 1986) proposes a sustained release diclofenac sodium preparation comprising rapid action diclofenac sodium combined with delayed action diclofenac sodium so that the action of diclofenac sodium can be sustained as long as possible. The delayed action component is disclosed as comprising diclofenac sodium covered with a coating of an enteric material or water-insoluble material. The enteric material used is a methacrylic acid-methyl methacrylate copolymer (including methacrylic acid copolymers S and L) which is soluble in water at an acidity level in the range of about pH 6-7. More particularly, the sustained release diclofenac sodium preparation is disclosed as comprising the rapid action component which is made by granulating diclofenac sodium with suitable excipient and binder into granules, and the delayed action component which is made by granulating diclofenac sodium with suitable excipient into granules, and coating the granules with an enteric material predominantly comprising a methacrylic acid-methyl methacrylate copolymer.

It was found that this sustained release diclofenac sodium preparation, especially comprising a delayed action component having an enteric coating of a methacrylic acidmethyl methacrylate copolymer can maintain diclofenac sodium in blood for an extended period of time as compared with conventional commercially available diclofenac sodium preparations. Making further research for the more efficient mass scale production of sustained release diclofenac sodium preparation, we found the following problems.

When the timed release diclofenac sodium preparation is produced in a mass scale, problems arise in the step of coating active component particles with an enteric material. The enteric coating tends to crack in the coating and subsequent drying steps. Coated particles tend to agglomerate and there is a chance for the coating to delaminate or chip away after agglomeration. Coated particles having a particle size in the desired range can be produced only in a limited yield. Once the enteric coating is cracked, chipped or peeled, the enteric component cannot exert its own function of retarding action because the diclofenac sodium of the enteric component will dissolve out before the coated particles reach the intestine. These defective particles fail to achieve the effect of sustaining the action of diclofenac sodium for a prolonged time. Thus, the sustained release diclofenac sodium preparation of the above-cited application is not suitable as such for mass production.

SUMMARY OF THE INVENTION

Therefore, an object of the present invention is to provide a long acting diclofenac sodium preparation which can maintain the action of diclofenac sodium for a prolonged time.

Another object of the present invention is to provide a long acting diclofenac sodium preparation which can be produced in a mass scale without inducing cracks in the enteric coating or causing agglomeration of coated particles and resultant coating delamination.

According to the present invention, there is provided a long acting diclofenac sodium preparation comprising a rapidly soluble component including an active ingredient consisting essentially of diclofenac sodium, and an enteric component including an active ingredient consisting essentially of diclofenac sodium and an enteric coating therefor, the enteric coating comprising in admixture 100 parts by weight of a methacrylic acid-methyl methacrylate copolymer, 3 to 40 parts by weight of a glycerin fatty acid ester, and 1 to 150 parts by weight of talc.

Preferably, the enteric coating is soluble in water at an acidity level in the range of about pH 6 to about pH 7, especially at about pH 7. Preferred examples of the methacrylic acid-methyl methacrylate copolymer include a copolymer soluble in water at about pH 7, that is, methacrylic acid copolymer S and a copolymer soluble in water at about pH 6, that is, methacrylic acid copolymer L. The weight ratio of the diclofenac sodium in the soluble component to the diclofenac sodium in the enteric component may be in the range of from about 6:4 to about 2:8, especially about 3:7. The enteric component may be in the form of beads, granules, fine granules, tablets, powder or microcapsules.

The long acting diclofenac sodium preparation comprising the rapidly soluble component combined with the enteric component may be in the form of beads, granules, fine granules, powder, tablets, capsules or divided dosage form thereof.

BRIEF DESCRIPTION OF THE DRAWINGS

The above and other objects, features, and advantages of the present invention will be better understood from the following description taken in conjunction with the accompanying drawings, in which.

DESCRIPTION OF THE PREFERRED EMBODIMENTS

Figure 1:
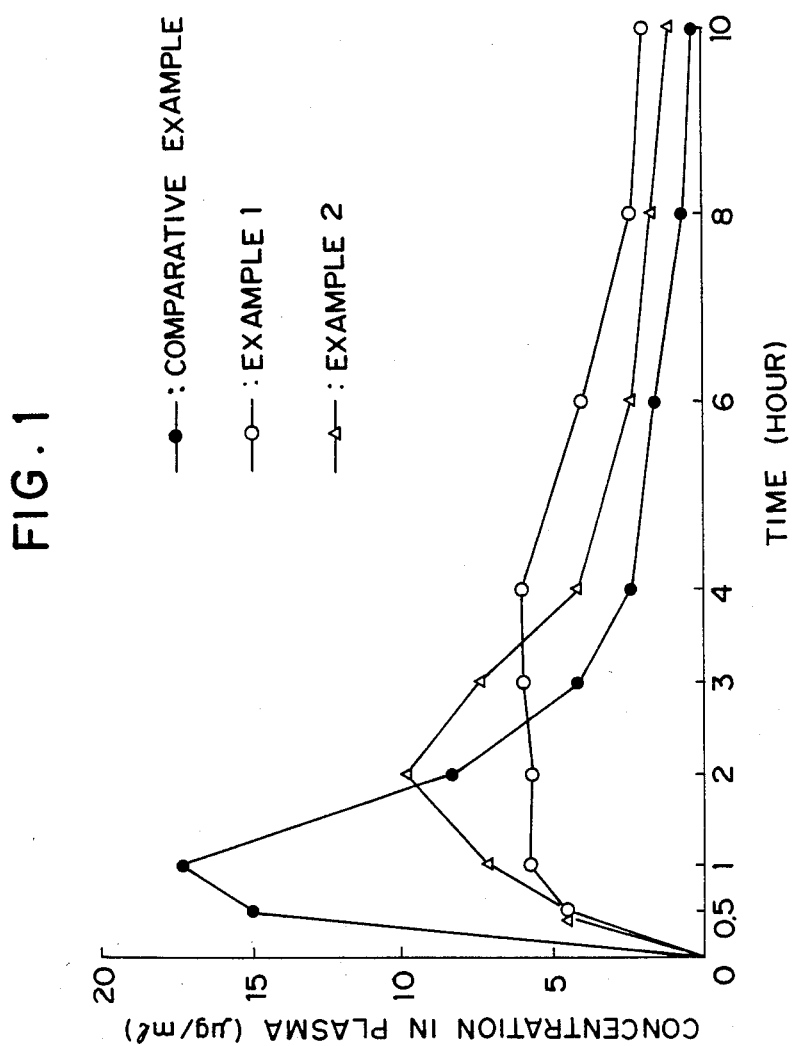
FIG. 1 is a diagram showing the concentration of diclofenac sodium in beagle dog plasma as a function of time in Experiment 1.

The long acting diclofenac sodium preparation of the present invention comprises a rapidly soluble component combined with an enteric component. The rapidly soluble component used herein means a diclofenac sodium preparation whose active ingredient consists essentially of diclofenac sodium and which has been subjected to none of sustained release and enteric coating treatments. More illustratively, the rapidly soluble component may be diclofenac sodium as such. It may also be a powder mixture of diclofenac sodium with suitable additives including binders, excipients, disintegrators, lubricants, coloring agents, and flavors. The powder or powder mixture may be either used in powder form or further granulated into beads, granules, and grains by any conventional granulating methods. The binders used herein include hydroxypropyl cellulose, polyvinyl pyrrolidone or povidone, acacia gum, and gelatin. The excipients used herein include starch, sucrose, lactose, mannitol, and dextrin. The disintegrators used herein include starch, carboxymethyl cellulose, calcium carboxymethyl cellulose, crystalline cellulose, and low substitution hydroxypropyl cellulose. The lubricants used herein include talc and magnesium stearate.

The enteric component has an active ingredient consisting essentially of diclofenac sodium and an enteric coating covering the active ingredient. More particularly, the enteric component is obtained by processing diclofenac sodium powder or a mixture thereof with a suitable additive or additives into microcapsules by any well-known methods, or processing diclofenac sodium powder or a mixture thereof with a suitable binder, excipient, disintegrator, lubricant, flavor and coloring agent into beads, granules, fine granules, tablets, or powder by any well-known methods, and then applying an enteric coating material thereto. The binder, excipient, disintegrator, and lubricant used herein may be selected from the examples described above for the soluble component.

The enteric coating applied to the enteric component is formed from a coating composition comprising a major proportion of a methacrylic acid-methyl methacrylate copolymer, a glycerin fatty acid ester mainly as a plasticizer, and talc mainly as an anti-adhesion agent. Any other additives including coloring agents, flavors and extenders may be added if desired.

Typical examples of the methacrylic acid-methyl methacrylate copolymer are methacrylic acid copolymer S soluble in water at about pH 7 (commercially available under the tradename Eudragit S100 from Rohm Pharma GmbH) and methacrylic acid copolymer L soluble in water at about pH 6 (commercially available under the tradename Eudragit L100 from Rohm Pharma GmbH), with the former being most preferred. Methacrylic acid copolymers L and S are defined in the Standards for Ingredients of Drugs not in the Japanese Pharmacopeia, 1986, as methacrylic acid-methyl methacrylate copolymers containing 38.0–52.0% and 25.0–34.5% of methacrylic acid on dried basis, respectively. They correspond to methacrylic acid copolymers A and B which are defined in the United States Pharmacopeia, 21st Revision, 1985, as methacrylic acid-methacrylic ester copolymers containing 46.0–50.6% and 27.6–30.7% of methacrylic acid on dried basis, respectively.

Talc generally serves to impart a proper thickness to the enteric coating to reinforce the coating and prevent coalescence of coated particles, thereby preventing delamination of the coating due to adhesion of coated particles and eventually increasing the percent yield of coated particles having a particle size within the desired range.

The glycerin fatty acid ester is a plasticizer for imparting flexibility to the coating, thereby preventing the coating from cracking during the process. Further, in cooperation with the methacrylic acid-methyl methacrylate copolymer used in the coating as an enteric coating base, the glycerin fatty acid ester and talc function to improve the acid resistance of the coating to prevent the diclofenac sodium from being dissolved out of the enteric component in gastric fluid, ensuring that the diclofenac sodium is released from the enteric component into intestinal fluid. More illustratively, the glycerin fatty acid ester imparts water resistance to the enteric component for an adequate time immediately after oral administration whereas the talc imparts such water permeability to the enteric coating that the enteric coating may be dissolved in the digestive tract, mainly intestine after oral administration, ensuring that the diclofenac sodium is released from the enteric component into intestinal fluid. Examples of the glycerin fatty acid ester include acetylated monoglycerides (distilled) commercially available as MYVACET® Type 9-40 from Distillation Products Industries Div. of Eastman Kodak Co. and glyceryl monostearate commercially available as NIKKOL® MGS-B from Nikko Chemicals K.K.

To achieve the timely release and other purposes as mentioned above, the ingredients should be blended such that 3 to 40 parts by weight of glycerin fatty acid ester and 1 to 150 parts by weight of talc are present per 100 parts by weight of methacrylic acid-methyl methacrylate copolymer. Below the lower limits, the glycerin fatty acid ester and talc are ineffective for the above-mentioned purposes. The presence of more than 150 parts of talc per 100 parts of the copolymer will lower the acid resistance of the coating. No additional effect is obtained when the glycerin fatty acid ester is used in excess of 40 parts per 100 parts of the copolymer.

The amount of the enteric composition coated varies depending on the type of preparation and the coating method although it generally ranges from 10 to 80% by weight based on the entire enteric component. In the case of spherical granules, better results are obtained when the coating amount ranges from 20 to 50% by weight based on the entire enteric component. The coating method is not critical to the present invention. In general, spray coating using a fluidized bed apparatus and manual coating using a coating pan are employed.

The long acting diclofenac sodium preparation of the present invention is produced by mixing the soluble and enteric components both mentioned above, dividing the mixture into unit doses or fractions of the unit dose, and optionally enclosing them into capsules. The preparation may be obtained as double coated granules having the soluble component coated on the outside of the enteric component or as tablets having the enteric component contained therein. The double coated granules are readily obtained by applying the rapidly soluble component powder on cores of the enteric component. The tablets are obtained by mixing the soluble and enteric components and an optional excipient and compression molding the mixture.

The weight ratio of the diclofenac sodium in the soluble component to the diclofenac sodium in the enteric component is somewhat critical to the present invention. To achieve a rapid rise of diclofenac sodium concentration in blood immediately after administration and maintenance of a sufficient blood concentration over an extended period of time after administration, the weight ratio of the diclofenac sodium in the soluble component to the diclofenac sodium in the enteric component should preferably be in the range of from about 6:4 to about 2:8. Most preferably the diclofenac sodium in the soluble component and the diclofenac sodium in the enteric component are present at a weight ratio of about 3:7.

The long acting diclofenac sodium preparation of the present invention not only quickly provides a pharmaceutical action at the initial due to the soluble component, but also provides a prolonged action lately due to the enteric component so that it can achieve an equivalent effect in a reduced number of administration as compared with the conventional preparation. The maximum blood concentration is relatively reduced, causing less side effects.

Since the enteric coating of the enteric component is formed from a composition comprising a major proportion of a methacrylic acid-methyl methacrylate copolymer and minor, but effective proportions of glycerin fatty acid ester and talc, few cracks occur in the enteric coating in the coating step and coated particles would scarecely adhere or agglomerate, preventing delamination of the enteric coating due to adhesion and eventually increasing the percent yield of acceptably coated particles. Thus the long acting diclofenac sodium preparation of the present invnetion can be commercially produced in a mass scale.

EXAMPLES

Examples of the present invention are given below by way of illustration and not by way of limitation.

Example 1

Preparation of plain granules A

A powder mixture was obtained by homogeneously blending 4200 grams of diclofenac sodium and 2280 grams of corn starch and finely dividing the blend. In a coating pan was admitted 3360 grams of sucrose within the range of 24-28 mesh. Using a spray gun, a solution of 201.6 grams of hydroxypropyl cellulose in 3830.4 grams of ethyl alcohol was sprayed over the sucrose to evenly wet the sucrose. The powder mixture was introduced into the pan to effect granulation by tumbling, obtaining spherical granules. The granules were dried at 55° C. for 3 hours. Plain granule fraction A of diclofenac sodium was obtained from the dry granules by removing a fraction not passing a 14-mesh screen (14-mesh oversize fraction) and a fraction passing a 32-mesh screen (32-mesh through fraction).

Preparation of enteric component B

A 5000-g portion of the above-prepared plain granule fraction A was introduced into a coating apparatus with a fluidized bed. A coating liquid having the composition shown in Table 1 was spray coated on the granules in a conventional manner until the coated granules reached a total weight of about 6250 grams. An enteric component B was obtained from the coated granules by removing 14-mesh oversize and 32-mesh through fractions. Enteric component B had a coating which was soluble at about pH 7.

TABLE 1

| Composition | |
|---|---|
| Methacrylic acid copolymer S | 1300 g |
| Glycerin fatty acid ester | 100 g |
| Talc | 40 g |
| Ethyl alcohol | 17200 g |
| Purified water | 1360 g |
| Total | 20000 g |

Preparation of rapidly soluble component C

A powder mixture was obtained by homogeneously blending 900 grams of diclofenac sodium, 3619.2 grams of corn starch, and 2532 grams of sucrose and finely dividing the blend. In a coating pan was admitted 3600 grams of sucrose in the range of 24-28 mesh. Using a spray gun, a solution of 152.8 grams of hydroxypropyl cellulose in 2903.2 grams of ethyl alcohol was sprayed over the sucrose to evenly wet the sucrose. The powder mixture was introduced into the pan to effect granulation by tumbling, obtaining spherical granules. The granules were dried at 55° C. for 3 hours. Rapidly soluble component C was obtained from the dry granules by removing 14-mesh oversize and 32-mesh through fractions.

Preparation of long acting diclofenac sodium preparation D

Long acting diclofenac sodium preparation D in hard gelatin capsule form according to the present invention was prepared by homogeneously mixing 1350.5 grams of soluble component C, 784.5 grams of enteric component B, and 15 grams of talc and filling capsules each with 287 mg of the mixture. This long acting diclofenac sodium preparation D contained a total amount of 50 mg of diclofenac sodium per capsule, with the weight ratio of diclofenac sodium in the soluble to enteric components being 3:7.

Example 2

Preparation of plain granules E

Plain granule fraction E of diclofenac sodium was obtained by the same procedure as the "preparation of plain granules A" in Example 1.

Preparation of enteric component F

A 5000-g portion of the above-prepared plain granule fraction E was introduced into a coating apparatus with a fluidized bed. A coating liquid having the composition shown in Table 2 was spray coated on the granules in a conventional manner until the coated granules reached a total weight of about 6250 grams. An enteric component F was obtained from the coated granules by removing 14-mesh oversize and 32-mesh through fractions. Enteric component F had a coating which was soluble at about pH 6.

TABLE 2

| Composition | |
|---|---|
| Methacrylic acid copolymer L | 1300 g |
| Glycerin fatty acid ester | 100 g |
| Talc | 40 g |
| Ethyl alcohol | 17200 g |
| Purified water | 1360 g |

TABLE 2-continued

| Composition | |
|---|---|
| Total | 20000 g |

Preparation of rapidly soluble component G

Rapidly soluble component G was obtained by the same procedure as the "preparation of rapidly soluble component C" in Example 1.

Preparation of long acting diclofenac sodium preparation H

Long acting diclofenac sodium preparation H in hard gelatin capsule form according to the present invention was prepared by homogeneously mixing 1350.5 grams of soluble component G, 784.5 grams of enteric component F, and 15 grams of talc into a granular mixture and filling capsules each with 287 mg of the granular mixture. This long acting diclofenac sodium preparation H contained a total amount of 50 mg of diclofenac sodium per capsule, with the weight ratio of diclofenac sodium in the soluble to enteric components being 3:7.

Example 3

Preparation of long acting diclofenac sodium preparation I

A powder mixture was obtained by homogeneously blending 562.5 grams of diclofenac sodium and 562.5 grams of corn starch and finely dividing the blend. In a coating pan was admitted 3922.5 grams of an enteric component which was prepared by the same procedure as the "preparation of enteric component B" in Example 1. Using a spray gun, a solution of 40 grams of hydroxypropyl cellulose in 760 grams of ethyl alcohol was sprayed over the enteric component granules to evenly wet them. The powder mixture was introduced into the pan to effect coating granulation by tumbling, obtaining spherical granules. The granules were dried at 55° C. for 3 hours. There was obtained long acting diclofenac sodium preparation I in double-coated granule form according to the present invention which contained 36.9% by weight of diclofenac sodium per granule, with the weight ratio of diclofenac sodium in the soluble to enteric components being 3.7.

Example 4

Preparation of long acting diclofenac sodium preparation J

Long acting diclofenac sodium preparation J in hard gelatin capsule form according to the present invention was prepared by homogeneously mixing 1350.5 grams of a rapidly soluble component which was prepared by the same procedure as the "preparation of rapidly soluble component C" in Example 1, 784.5 grams of an enteric component which was prepared by the same procedure as the "preparation of enteric component B" in Example 1, and 15 grams of talc into a granular mixture and filling capsules each with 215 mg of the granular mixture. This long acting diclofenac sodium preparation J contained a total amount of 37.5 mg of diclofenac sodium per capsule, with the weight ratio of diclofenac sodium in the soluble to enteric components being 3:7.

Comparative Example

Preparation of rapid action diclofenac sodium preparation K

For comparison purposes, rapid action diclofenac sodium preparation K in hard gelatin capsule form was prepared by homogeneously mixing 1255.2 grams of plain granules which were prepared by the same procedure as the "preparation of plain granules A" in Example 1 and 5 grams of talc into a granular mixture and filling capsules each with 120 mg of the granular mixture. This rapid action diclofenac sodium preparation K contained 50 mg of diclofenac sodium per capsule.

Experiment 1

Pharmacokinetic Test On Beagle

One capsule of each of long acting diclofenac sodium preparations D and H obtained in Examples 1 and 2 and rapid action diclofenac sodium preparation K obtained in Comparative Example was orally administered along with 30 ml of water to a beagle dog who had been fasted overnight. It was determined how the concentration of diclofenac in plasma varied with a lapse of time. A measure diclofenac concentration was converted into a concentration of diclofenac sodium. The results are shown in FIG. 1.

As seen from FIG. 1, long acting diclofenac sodium preparations D and H of Examples 1 and 2 maintain the blood concentration for a significantly extended period of time as compared with rapid action diclofenac sodium preparation K of Comparative Example (which was substantially the same as the commercially available diclofenac sodium preparation). It is also seen that long acting diclofenac sodium preparation D of Example 1 using methacrylic acid copolymer S as the base of the enteric coating of its enteric component exhibits more prolonged action than long acting diclofenac sodium preparation H of Example 2 using methacrylic acid copolymer L as the base of the enteric coating of its enteric component.

Experiment 2

Pharmacokinetic Test On Human

One capsule of long acting diclofenac sodium preparation D of Example 1 and one tablet of a conventional diclofenac sodium preparation were orally administered to healthy adult men who had been fasted overnight. It was determined how the concentration of diclofenac in plasma varied with a lapse of time. The results are shown in FIG. 2.

Figure 2:
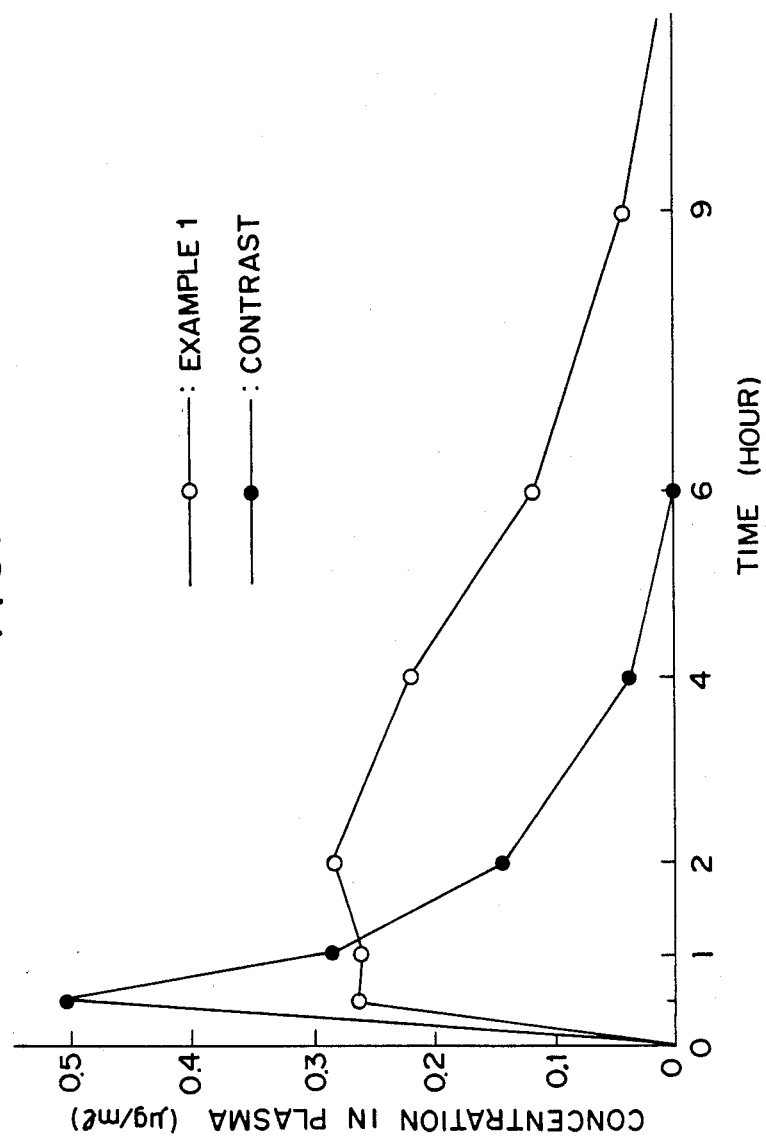
FIG. 2 is a diagram showing the concentration of diclofenac sodium in human plasma as a function of time in Experiment 2.

As seen from FIG. 2, long acting diclofenac sodium preparation D of Example 1 exhibited prolonged action.

It is to be noted that the conventional diclofenac sodium preparation used herein is one containing 25 mg of diclofenac sodium per tablet commercially available as "Voltaren" from Ciba Geigy and corresponds to the rapid action preparation as used in the present invention.

Experiment 3

Talc Content of Enteric Coating

Into a fluidized bed coating apparatus was introduced 5000 grams of plain granules which were prepared by the same procedure as the "preparation of plain granules A" in Example 1. A coating liquid having the composition shown in Table 3 was spray coated on the granules in a conventional manner until the coated granules reached a total weight of about 6250 grams.

TABLE 3

| Ingredients, gram | Coating Composition | | | | |
|---|---|---|---|---|---|
| | L-1 | L-2 | L-3 | L-4 | L-5 |
| Methacrylic acid copolymer S | 1300 | 1300 | 1300 | 1300 | 1300 |
| Glycerin fatty acid ester | 100 | 100 | 100 | 100 | 100 |
| Talc | 0 | 6.5 | 13 | 26 | 52 |
| Ethyl alcohol | 17200 | 17200 | 17200 | 17200 | 17200 |
| Purified water | 1360 | 1360 | 1360 | 1360 | 1360 |
| Total (g) | 19960 | 19966.5 | 19973 | 19986 | 20012 |

An enteric component was obtained from the coated granules by removing 14-mesh oversize and 32-mesh through fraction. The enteric component was weighed to calculate the percent yield. The results are shown in Table 4. It is seen that the percent yield of enteric granules within the desire size is substantially increased by blending at least 1 part by weight of talc to 100 part by weight of methacrylic acid copolymer S.

TABLE 4

| | L-1 | L-2 | L-3 | L-4 | L-5 |
|---|---|---|---|---|---|
| Talc content* | 0 | 0.5 | 1 | 2 | 4 |
| Yield, % | 71.5 | 81.3 | 94.2 | 97.8 | 97.5 |

*parts by weight per 100 parts of methacrylic acid copolymer S

Experiment 4

Glycerin Fatty Acid Ester Content in Enteric Coating

Into a fluidized bed coating apparatus was introduced 5000 grams of plain granules which were prepared by the same procedure as the "preparation of plain granules A" in Example 1. A coating liquid having the composition shown in Table 5 was spray coated on the granules in a conventional manner until the coated granules reached a total weight of about 6250 grams.

TABLE 5

| Ingredients, gram | Coating Composition | | | |
|---|---|---|---|---|
| | M-1 | M-2 | M-3 | M-4 |
| Methacrylic acid copolymer S | 1300 | 1300 | 1300 | 1300 |
| Glycerin fatty acid ester | 0 | 13 | 39 | 65 |
| Talc | 40 | 40 | 40 | 40 |
| Ethyl alcohol | 17200 | 17200 | 17200 | 17200 |
| Purified water | 1360 | 1360 | 1360 | 1360 |
| Total (g) | 19900 | 19913 | 19939 | 19965 |
| Ingredients, gram | M-5 | M-6 | M-7 | M-8 |
| Methacrylic acid copolymer S | 1300 | 1300 | 1300 | 1300 |
| Glycerin fatty acid ester | 130 | 260 | 390 | 520 |
| Talc | 40 | 40 | 40 | 40 |
| Ethyl alcohol | 17200 | 17200 | 17200 | 17200 |
| Purified water | 1360 | 1360 | 1360 | 1360 |
| Total (g) | 20030 | 20160 | 20290 | 20420 |

Enteric components M-1 through M-8 were obtained from the coated granules by removing 14-mesh oversize and 32-mesh through fractions. Enteric components M-1 through M-8 were determined for acid resistance by the second procedure (rotating paddle procedure) of the dissolving test prescribed in the Japan Pharmacopoeia, 11th Edition. The coated granules were placed in 900 ml of a test solution at pH 4.5. The solution was paddled at 37° C and 100 rpm. to determine the amount of diclofenac sodium dissolved out after 30 minutes. The results are shown in Table 6. The proportion of diclofenac sodium dissolved out is the percentage of the amount of diclofenac sodium dissolved out based on the initial amount of diclofenac sodium contained.

TABLE 6

Glycerin fatty acid ester content vs. Amount of diclofenac sodium dissolved

| Composition | M-1 | M-2 | M-3 | M-4 | M-5 | M-6 | M-7 | M-8 |
|---|---|---|---|---|---|---|---|---|
| Glycerin fatty acid ester* | 0 | 1 | 3 | 5 | 10 | 20 | 30 | 40 |
| Proportion of diclofenac sodium dissolved (wt. %) | | | | | | | | |
| Test No. 1 | 38.5 | 15.8 | 4.8 | 3.8 | 0.8 | 2.6 | 1.5 | 2.5 |
| 2 | 46.7 | 10.6 | 7.3 | 2.2 | 1.2 | 1.8 | 0.8 | 8.8 |
| 3 | 36.9 | 21.0 | 3.2 | 1.8 | 0.7 | 1.5 | 4.1 | 7.3 |
| 4 | 44.9 | 17.4 | 2.5 | 2.9 | 0.3 | 0.2 | 2.7 | 6.9 |
| 5 | 29.0 | 16.2 | 7.9 | 1.2 | 0.8 | 2.1 | 1.3 | 4.2 |
| 6 | 40.3 | 9.5 | 4.0 | 0.7 | 3.1 | 0.9 | 2.9 | 7.5 |
| Average | 39.38 | 15.08 | 4.95 | 2.10 | 1.15 | 1.52 | 2.21 | 6.20 |
| S.D.± | 6.32 | 4.32 | 2.20 | 1.13 | 1.00 | 0.86 | 1.23 | 2.35 |

*parts by weight per 100 parts of mathacrylic acid copolymer S
S.D.: standard deviation It is seen that diclofenac sodium dissolves out little, that is, acid resistance is maintained when 3 to 40 parts by weight of glycerin fatty acid ester is blended to 100 parts by weight of methacrylic acid copolymer S.

Experiment 5

Chronic rheumarthritis treatment

The cases tested were patients who had suffered from rheumarthritis for at least 6 months and were diagnosed to belong to Classical or Definite RA according to the American Rheumatism Associate (ARA) diagnosis standard. The drugs tested were long acting diclofenac sodium preparation J of Example 4 of the invention (containing 37.5 mg of diclofenac sodium per capsule) and the conventional diclofenac sodium preparation (containing 25 mg of diclofenac sodium per tablet, see Experiment 2). A group comparison study was performed by the double blind test procedure. The results are shown in Tables 7 and 8.

TABLE 7

Final Global Improvement

| | Group A | | Group B | |
|---|---|---|---|---|
| | Case | Cum. | Case | Cum. |
| Markedly improved | 3 | 3.4% | 3 | 3.5% |
| Improved | 23 | 29.9% | 17 | 23.3% |
| Slightly improved | 27 | 60.9% | 18 | 44.2% |
| Unchanged | 21 | 85.1% | 33 | 82.6% |
| Slightly aggravated | 9 | 95.4% | 10 | 94.2% |
| Aggravated | 2 | 97.7% | 4 | 98.8% |
| Markedly aggravated | 2 | 100.0% | 1 | 100.0% |
| Total | 87 | | 86 | |

Group A: long acting diclofenac sodium preparation of the invention
Group B: commercially available preparation

TABLE 8

Type and Frequency of Side Effects

| | Group A | | Group B | |
|---|---|---|---|---|
| Cases observed | 99 | | 98 | |
| Cases with side effects | 12 | (12.1%) | 21 | (21.4%) |
| symptom of digestive tract | 6 | (6.0%) | 14 | (14.3%) |
| symptom of central nervus | 0 | (0%) | 2 | (2.0%) |
| skin | 1 | (1.0%) | 4 | (4.1%) |
| edema | 2 | (2.0%) | 0 | (0%) |
| others | 2 | (2.0%) | 2 | (2.0%) |
| abnormal values in laboratory data | 1 | (1.0%) | 3 | (3.1%) |

TABLE 8-continued

| Type and Frequency of Side Effects | | |
|---|---|---|
| | Group A | Group B |
| Number of instances of side effects | 12 | 25 |

Group A: long acting diclofenac sodium preparation of the invention
Group B: commercially available preparation As seen from a comparison between the administration of two capsules per day of the present preparation each containing 37.5 mg of diclofenac sodium and the administration of three tablets per day of the commercially available preparation each containing 25 mg of diclofenac sodium, the present preparation exhibits a high percent improvement despite no significant difference in the final global improvement and a lower percent appearance of sideeffects. Thus the present preparation is superior to the commercially available preparation with respect to effectiveness and safeness.

Experiment 6

Single dose against postoperative pain

The cases tested were patients who suffered from postoperative pain in a plastic surgery field. The drugs tested were long acting diclofenac sodium preparation J of Example 4 of the invention (containing 37.5 mg of diclofenac sodium per capsule) and the conventional diclofenac sodium preparation (containing 25 mg of diclofenac sodium per tablet, see Experiment 2). A group comparison study was performed by the double blind test procedure. The overall percent improvement results evaluated at varying times are shown in Table 9.

With respect to the overall percent improvement, no significant difference was observed between the two groups at 1, 2 and 4 hours after administration, but a difference was observed at 6 and 8 hours after administration, and a significant difference was observed at 10 hours after administration. In all cases, the present preparation provided a higher percent amelioration than the commercially available preparation.

The present preparation maintained its action of mitigating the postoperative pain over 6 hours and longer after administration of a single dose. It was observed that the present preparation had long lasting action.

Japanese Patent Application Kokai No. 61-44811 previously cited discloses several materials useful as the plasticizer for the enteric coating, including Polisorbate 80, castor oil, Macrogol 400-6000, Triacetine, dimethyl phthalate, dibutyl phthalate, and propylene glycol as well as glycerin fatty acid esters. These materials other than glycerin fatty acid esters are undesirable as the plasticizer for the enteric coating of the enteric component of the long acting diclofenac sodium preparation according to the present invention because they are toxic or potentially toxic, pharmaceutically active, or water soluble as shown in Table 10.

TABLE 10

| | Pharmaceutical | | |
|---|---|---|---|
| | Toxic | Active | Soluble |
| Glycerin fatty acid ester | — | — | — |
| Polisorbate 80 | — | — | X |
| Castor oil | — | X | — |
| Macrogol 400-6000 | — | — | X |
| Triacetine | — | — | X |
| Dimethyl phthalate | X | X | X |
| Dibutyl phthalate | X | X | — |
| Propylene glycol | — | — | X |

*X indicates that the material is toxic, active or water soluble.

As seen from Table 10, phthalic acid esters including dimethyl phthalate and dibutyl phthalate are undesired because they are toxic or potentially toxic. Castor oil, dimethyl phthalate and dibutyl phthalate are undesired because they are pharmaceutically active. Castor oil is a drastic purgative, and dimethyl phthalate and dibutyl phthalate are repellents against blood-sucking insects. Those materials having water-soluble nature are undesired because enteric coatings containing them tend to allow more or less diclofenac sodium to dissolve in

TABLE 9

| Time evaluated after administration | Drug | | Improvement with time | | | | | | Total | * |
|---|---|---|---|---|---|---|---|---|---|---|
| | | | Markedly improved | Im-proved | Slightly improved | Unchanged | Slightly aggravated | Aggra-vated | Markedly aggravated | | |
| 1 hour | A | Case | 3 | 6 | 27 | 26 | 2 | 0 | 0 | 64 | $t(\infty)$ |
| | | Cum. % | 4.7 | 14.1 | 56.3 | 96.9 | 100.0 | | | | = 0.684 |
| | B | Case | 1 | 8 | 24 | 30 | 3 | 0 | 0 | 66 | N.S. |
| | | Cum. % | 1.5 | 13.6 | 50.0 | 95.5 | 100.0 | | | | |
| 2 hour | A | Case | 6 | 16 | 25 | 16 | 1 | 1 | 0 | 65 | $t(\infty)$ |
| | | Cum. % | 9.2 | 33.8 | 72.3 | 96.9 | 98.5 | 100.0 | | | = 0.588 |
| | B | Case | 3 | 15 | 26 | 15 | 3 | 0 | 0 | 62 | N.S. |
| | | Cum. % | 4.8 | 29.0 | 71.0 | 95.5 | 100.0 | | | | |
| 4 hour | A | Case | 12 | 22 | 14 | 10 | 0 | 0 | 0 | 58 | $t(\infty)$ |
| | | Cum. % | 20.7 | 58.6 | 82.8 | 100.0 | | | | | = 1.137 |
| | B | Case | 6 | 23 | 19 | 9 | 1 | 0 | 0 | 58 | N.S. |
| | | Cum. % | 10.3 | 50.0 | 82.8 | 98.3 | 100.0 | | | | |
| 6 hour | A | Case | 18 | 20 | 11 | 5 | 0 | 0 | 0 | 54 | $t(\infty)$ |
| | | Cum. % | 33.3 | 70.4 | 90.7 | 100.0 | | | | | = 1.774 |
| | B | Case | 10 | 21 | 19 | 4 | 1 | 0 | 0 | 55 | |
| | | Cum. % | 18.2 | 56.4 | 90.9 | 98.2 | 100.0 | | | | |
| 8 hour | A | Case | 21 | 15 | 13 | 3 | 0 | 0 | 0 | 52 | $t(\infty)$ |
| | | Cum. % | 40.4 | 69.2 | 94.2 | 100.0 | | | | | = 1.886 |
| | B | Case | 12 | 19 | 15 | 6 | 1 | 0 | 0 | 53 | |
| | | Cum. % | 22.6 | 58.5 | 86.8 | 98.1 | 100.0 | | | | |
| 10 hour | A | Case | 21 | 15 | 9 | 3 | 0 | 0 | 0 | 48 | $t(\infty)$ |
| | | Cum. % | 43.8 | 75.0 | 93.8 | 100.0 | | | | | = 2.132 |
| | B | Case | 12 | 17 | 14 | 5 | 1 | 0 | 0 | 49 | |
| | | Cum. % | 24.5 | 59.2 | 87.7 | 98.0 | 100.0 | | | | |

A: Long acting diclofenac preparation of invention
B: Conventional preparation
*Wilcoxon paired comparison distribution (rank sum)   : $p < 0.05$   : $p < 0.10$ N.S.: Not Significant gastric fluid. Although the enteric coating should not be dissolved in gastric fluid, the use of a water-soluble plasticizer would result in an enteric coating which is likely to be dissolved away in the stomach, that is, less resistant to acid.

A further test was carried out to examine the acid resistance of an enteric component containing a water-soluble plasticizer, Macrogol 6000 and an enteric component containing a water-insoluble plasticizer, glycerin fatty acid ester. This is reported in Experiment 7.

Experiment 7

Examination of Plasticizers

Into a fluidized bed coating apparatus was introduced 5000 grams of plain granules which were prepared by the same procedure as the "preparation of plain granules A" in Example 1. A coating liquid having the composition shown in Table 11 was spray coated on the granules in a conventional manner until the coated granules reached a total weight of about 6250 grams.

TABLE 11

| Composition | |
|---|---|
| Methacrylic acid copolymer S | 1300 g |
| Macrogol 6000 | 100 g |
| Talc | 40 g |
| Ethyl alcohol | 17200 g |
| Purified water | 1360 g |
| Total | 20000 g |

An enteric component N was obtained from the coated granules by removing 14-mesh oversize and 32-mesh through fractions. This enteric component N and enteric component B of Example 1 were determined for acid resistance by the second procedure (rotating paddle procedure) of the dissolving test prescribed in the Japan Pharmacopoeia, 11th Edition. The coated granules were placed in 900 ml of a test solution at pH 4.5. The solution was paddled at 37° C. and 100 rpm. to determine the amount of diclofenac sodium dissolved out. The results are shown in Table 12.

TABLE 12

| | Enteric Component | |
|---|---|---|
| | B | N |
| Plasticizer | Glycerine fatty acid ester | Macrogol 6000 |
| Percentage of diclofenac sodium dissolved (wt. %) | | |
| Time (hour) | | |
| 0.5 | 1.1 | 4.9 |
| 1.0 | 2.9 | 11.9 |
| 1.5 | 4.1 | 19.3 |
| 2.0 | 5.5 | 27.0 |

It is seen that acid resistance is maintained when the glycerin fatty acid ester is used. Less acid resistance is achieved when the water-soluble plasticizer, Macrogol 6000 is used.

We claim:

1. A long acting diclofenac sodium preparation comprising
 a rapidly soluble component including an active ingredient consisting essentially of diclofenac sodium, and
 an enteric component including an active ingredient consisting essentially of diclofenac sodium and an enteric coating therefor, said enteric coating consisting essentially of in admixture 100 parts by weight of a methacrylic acid-methyl methacrylate copolymer, 3 to 40 parts by weight of a glycerin fatty acid ester, and 1 to 150 parts by weight of talc.

2. The long acting diclofenac sodium preparation of claim 1 wherein said enteric coating is soluble in water at an acidity level in the range of about pH 6 to about pH 7.

3. The long acting diclofenac sodium preparation of claim 1 wherein said enteric coating is soluble at about pH 7.

4. The long acting diclofenac sodium preparation of claim 1 wherein said methacrylic acid-methyl methacrylate copolymer is methacrylic acid copolymer S.

5. The long acting diclofenac sodium preparation of claim 1 wherein said methacrylic acid-methyl methacrylate copolymer is methacrylic acid copolymer L.

6. The long acting diclofenac sodium preparation of claim 1 wherein the weight ratio of the diclofenac sodium in the soluble component to the diclofenac sodium in the enteric component is in the range of from about 6:4 to about 2:8.

7. The long acting diclofenac sodium preparation of claim 1 wherein the weight ratio of the diclofenac sodium in the soluble component to the diclofenac sodium in the enteric component is about 3:7.

8. The long acting diclofenac sodium preparation of claim 1 wherein the enteric component is in the form of beads, granules, fine granules, tablets, powder or microcapsules.

9. The long acting diclofenac sodium preparation of claim 1 which is in the form of beads, granules, fine granules, powder, tablets, capsules or divided dosage form thereof.

* * * * *